United States Patent
Jackels et al.

(10) Patent No.: US 9,914,149 B2
(45) Date of Patent: Mar. 13, 2018

(54) PROCESS AND APPARATUS FOR SUPPLY OF PARTICULATE MATERIAL TO A PARTICULATE PRINTING PROCESS

(71) Applicant: The Procter & Gamble Company, Cincinnati, OH (US)

(72) Inventors: Hans Adolf Jackels, Mechernich (DE); Meike Richter, Euskirchen (DE); Walter Pieter Hendrik Laurentius Van Der Klugt, Mechernich (DE)

(73) Assignee: The Procter & Gamble Company, Cincinnati, OH (US)

( * ) Notice: Subject to any disclaimer, the term of this patent is extended or adjusted under 35 U.S.C. 154(b) by 287 days.

(21) Appl. No.: 14/740,315

(22) Filed: Jun. 16, 2015

(65) Prior Publication Data
US 2015/0359683 A1    Dec. 17, 2015

(30) Foreign Application Priority Data

Jun. 17, 2014  (EP) .................................... 14172729

(51) Int. Cl.
| | |
|---|---|
| *B05C 19/06* | (2006.01) |
| *A61F 13/15* | (2006.01) |
| *B65G 65/48* | (2006.01) |
| *A61F 13/532* | (2006.01) |

(52) U.S. Cl.
CPC ........ *B05C 19/06* (2013.01); *A61F 13/15658* (2013.01); *A61F 13/5323* (2013.01); *B65G 65/4881* (2013.01); *A61F 2013/15821* (2013.01)

(58) Field of Classification Search
None
See application file for complete search history.

(56) References Cited

U.S. PATENT DOCUMENTS

| | | | | |
|---|---|---|---|---|
| 4,521,977 | A | * | 6/1985 | Graff .................... B29B 13/065 34/169 |
| 4,863,076 | A | | 9/1989 | Anderson et al. |
| 5,560,878 | A | * | 10/1996 | Dragoo ................. A61F 13/534 264/115 |
| 7,838,722 | B2 | | 11/2010 | Blessing et al. |

(Continued)

FOREIGN PATENT DOCUMENTS

| | | |
|---|---|---|
| EP | 1 621 165 A1 | 2/2006 |
| EP | 2 554 144 A1 | 2/2013 |

(Continued)

OTHER PUBLICATIONS

PCT International Search Report, dated Feb. 2, 2016, 11 pages.
EP International Search Report, dated Dec. 15, 2014, 5 pages.

*Primary Examiner* — Xiao S Zhao
(74) *Attorney, Agent, or Firm* — Sarah M. DeCristofaro

(57) ABSTRACT

A process and apparatus for depositing particulate material in a predetermined pattern onto a moving surface is disclosed. A particulate material may be fed under gravity from a hopper to a discharge zone containing a feed opening. A gas may be supplied, by a gas supply assembly, under pressure to the bulk of particulate material within the hopper discharge zone. The particulate material may be transferred through the feed opening to the surface of a transfer device, which contains a pattern of particulate-receiving recesses. The transfer device may rotate to a deposition zone and transfer the particulate material to a carrier layer.

20 Claims, 2 Drawing Sheets

(56) References Cited

U.S. PATENT DOCUMENTS

| | | |
|---|---|---|
| 8,590,582 B2 | 11/2013 | Jackels et al. |
| 2006/0024433 A1 | 2/2006 | Blessing et al. |
| 2011/0017398 A1 | 1/2011 | Blessing et al. |
| 2011/0130732 A1* | 6/2011 | Jackels ............ A61F 13/15658 604/365 |
| 2011/0297080 A1 | 12/2011 | Pastrello et al. |
| 2013/0062802 A1 | 3/2013 | Goda et al. |

FOREIGN PATENT DOCUMENTS

| | | |
|---|---|---|
| JP | 2010-246990 | 11/2010 |
| WO | WO 2010/103453 A1 | 9/2010 |

* cited by examiner

PROCESS AND APPARATUS FOR SUPPLY OF PARTICULATE MATERIAL TO A PARTICULATE PRINTING PROCESS

CROSS REFERENCE TO RELATED APPLICATION

This application claims priority to European Patent Application No. EP 14172729.7, filed Jun. 17, 2014.

FIELD OF THE INVENTION

The present disclosure relates to a process and apparatus for supplying a particulate material to a particulate printing process, in particular at high process speeds. The present disclosure is particularly applicable to processes and apparatus for laying down predetermined patterns of superabsorbent particulates in order to form an absorbent core suitable for use in absorbent articles such as diapers, infant training pants, incontinence products, feminine hygiene products, and sanitary napkins, for example.

BACKGROUND

Composite structures typically comprise an absorbent core for an absorbent product which has an absorbent particulate material that is immobilized when wet. The absorbent core comprises a substrate layer with an absorbent material, such as an absorbent polymer material.

U.S. Pat. No. 4,863,076, issued on Sep. 5, 1989, discloses an apparatus and method for feeding particulate material from an aerated hopper into a process stream at a controlled flow rate. Whilst the flow rate of particulate material is controlled, this process is not capable of delivering a profiled distribution of the particulate material into the subsequent stage of the process.

EP-A-1 621 165, published Feb. 1, 2006, discloses a process for producing absorbent structures. The process comprises the steps of pre-metering an amount of particulate material by means of a transfer device having recesses on the surface which, in number, size and position, determine the pattern of particulate material taken up by the transfer device; moving the transfer device between a loading position and a meeting position; and expelling the particulate material onto a carrier layer at the meeting position so that a profiled distribution of particulate material is retained on the carrier layer. However, at ever-increasing process speeds, reliable and consistent transfer of the particulate material from the hopper into the recesses of the transfer device becomes difficult. In this case the recesses may not be consistently filled to the same level each and every time they are filled below the hopper and the accuracy and reproducibility of the profiled distribution on the carrier layer may be compromised.

There remains a need for a process and apparatus to accurately and reproducibly provide a profiled distribution of a particulate material, in particular and absorbent particulate material, to a carrier layer, even in a high speed process.

SUMMARY OF THE INVENTION

The present disclosure relates to a process for depositing particulate material in a predetermined pattern onto a moving surface comprising the steps of: feeding the particulate material under gravity from a hopper to a discharge zone containing an feed opening; supplying a gas under pressure to the bulk of particulate material within the hopper discharge zone; transferring the particulate material through the feed opening to the surface of a transfer device, wherein the outer surface of the transfer device contains a pattern of particulate-receiving recesses; and rotating the transfer device to a deposition zone and transferring the particulate material to a carrier layer.

The present disclosure further relates to an apparatus. The apparatus may include a hopper including a discharge zone. The discharge zone may include a feed opening. Further, the discharge zone may include a gas supply assembly to supply gas under pressure into particulate material within the discharge zone. The apparatus may also include a transfer device adjacent to the feed opening, and the outer surface of the transfer device may contain a pattern of particulate-receiving recesses.

DETAILED DESCRIPTION

The present disclosure provides a profiled distribution of a particulate material which is accurate and reproducible even at high process speeds. Preferred embodiments are explained below with reference to the Figures.

Figure 1:
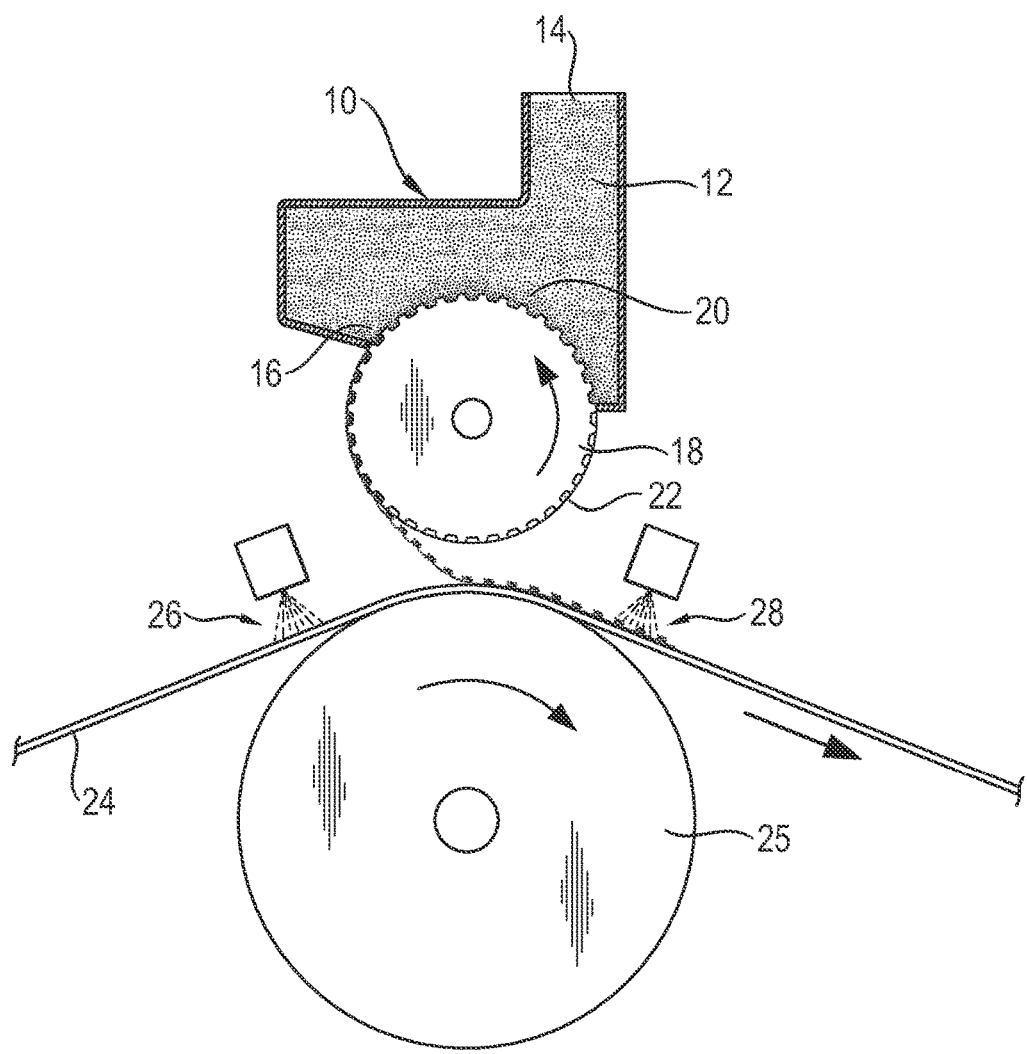
FIG. 1 is a schematic, side view of an apparatus according to one embodiment of the present disclosure.

FIG. 1 shows a hopper (10) filled with a bulk of particulate material (12). The hopper (10) has a supply opening (14) on the upper side and a delivery opening (16) at the bottom. The hopper forms one embodiment of what is called "bulk" in the present context.

A printing roll (18) enters into the opening (16) in the hopper (10) in a way that the bottom of the hopper surrounding the opening (16) closely follows the contour of the roller (18) and an unintended loss of particulate material is prevented.

The printing roll (18) is provided with holes or recesses (22) on the surface thereof which are filled with particulate material (12) from the discharge zone (20) of the bulk of particulate (12) in the hopper (10), while the surface of the roll (18) passes through the particulate material (12) inside the hopper (10). The number, the size and the position of the recesses (22) are selected such that the volume and the pattern of the recesses correspond to the intended pattern and distribution profile of the particulate material which is to be received by the printing roll and to be transferred to a carrier layer as will be explained below.

The printing roll (18) forms one embodiment of a transfer device according to the present disclosure. Another embodiment could for instance be formed by a belt having recesses in the surface thereof for receiving particulate material. Alternative methods of transferring the particulate material to the carrier layer may comprise air assisted transfer, transfer by centrifugal forces or electrical charge, for example. A rotatable printing roll is however a preferred embodiment as described in more detail, below.

The particulate material is taken up by the recesses (22) of the printing roll (18) when one or more of the recesses (22) on the transfer roll (18) are in this loading position. The absorbent material is retained in these recesses on the way from the hopper (10) to a position called the deposition zone, where the printing roll (18), which is rotated in a counter clockwise direction, as illustrated in FIG. 1, is in a position immediately adjacent the surface of a carrier layer (24). The carrier layer (24) is supported by a rotating support roll (25).

The carrier layer is, for instance, a web material onto which the absorbent material is deposited or laid down (such as by gravity) from the printing roll. For holding the absorbent material on the carrier layer (24), glue is applied, preferably slot-coated or sprayed, onto the carrier layer (24) upstream of the deposition zone between the printing roll (18) and the carrier layer (24), which upstream position is designated by reference numeral (26). Because the glue is applied in this upstream position (26) onto the carrier layer (24), the particulate material is retained on the carrier layer (24). Glue for retaining the absorbent material on the carrier layer (24) may be a hot melt adhesive material applied through nozzles such as are commercially available from Nordson Company, Dawsonville, Ga., USA.

The support roll (25), which could alternatively also be provided by a moving belt, may hold the absorbent material down onto the carrier, such as by use of a pressure differential (vacuum) through a screen forming the cylindrical surface of the support roll (25). In another position downstream the transfer position between the printing roll (18) and the carrier layer (24), which position is designated by (28), glue is, optionally, sprayed onto the particulate material on the carrier layer (24). The glue may be a microfilament glue entering like fibers between the granules of the particulate material to hold the whole deposit together. In one embodiment it is also possible to apply a cover layer carrying glue onto the particulate material.

It may be advantageous to use materials for the cylindrical support roll surface that have a low or no tendency to accumulate adhesive residue. This may be achieved by topological surface modification of surfaces (for instance at nano-scale), by ceramic coatings, or by a combination of both, e.g. Teflon™ coated surfaces or silicon rubber materials. For example, if the carrier layer (24) is exposed to a vacuum on the inside of the support roll, the surface of the support roll can be made of a silicon rubber screen, which may be metal reinforced.

According to the present disclosure, gas may be supplied under pressure to the bulk of particulate material within the hopper discharge zone. The gas assists the filling of the recesses.

Figure 2:
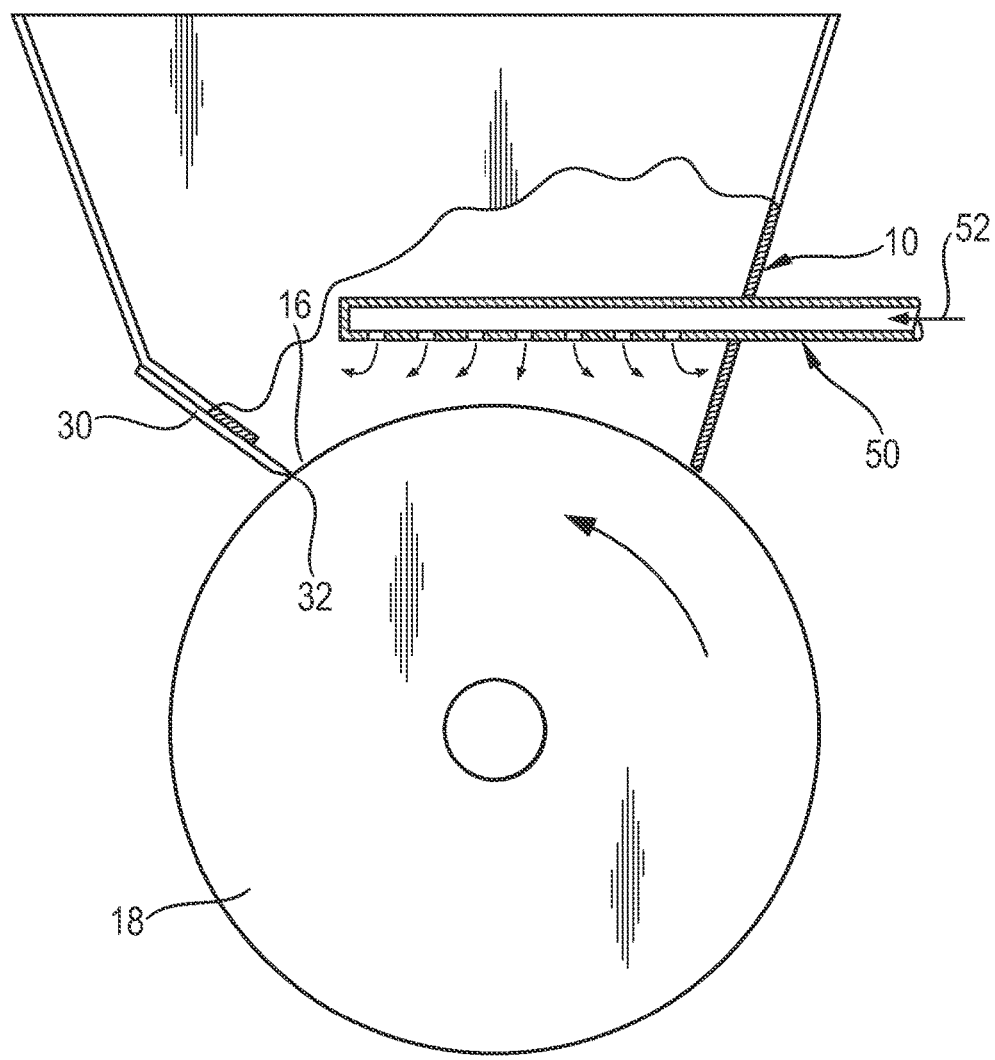
FIG. 2 is a schematic, side view of a portion of an apparatus according to an embodiment of the present disclosure.

FIG. 2 shows an enlarged view of the hopper (10) and the printing roll (18). A supply conduit (50) may supply gas (52) under pressure to the bulk of particulate material within the hopper discharge zone. The gas brings the particulate material to an expanded state and improves powder flowability in the hopper discharge zone. Preferably the gas is air, but other gasses could equally well be used. In the present invention this is referred to as air-assisted filling of the particulate material.

In an embodiment, the gas (52) may be supplied under pressure within the bulk of particulate material within the hopper (10). A conduit (50), such as a pipe, carries the gas through the wall of the hopper (10) and into the bulk of the particulate material, and the gas (52) exits the conduit (50) through suitable holes, e.g. nozzles, located within the bulk of particulate material.

Without being bound by theory it is believed that the feed rate of the particulate material varies across the width of the opening (16) in the machine direction (i.e. in the direction tangential to the rotation of the printing roll (18) at the opening (16)). In some areas across the width of the opening, the flow rate of particulate material may be reduced to very low rates, or even to zero ("stagnation"). This can lead to inaccurate and inconsistent filling of the recesses in the printing roll (18) especially at high process speeds. The introduction of the air-assisted filling gas (52) improves powder flowability which, in turn, causes more even flow rates of particulate material right across the width of the opening (16).

There is a certain risk that additional particulate material beyond those filling the recesses are carried out of the hopper between the surface of the printing roll (18) and adjacent edge of the bottom of the hopper. Thus, a scraping means (32) may be provided at the edge of the bottom of the hopper as shown in FIG. 2.

As used herein the following terms have the following meanings:

"Absorbent article" refers to devices that absorb and contain liquid, and more specifically, refers to devices that are placed against or in proximity to the body of the wearer to absorb and contain the various exudates discharged from the body. Absorbent articles include but are not limited to diapers, adult incontinence briefs, training pants, diaper holders and liners, sanitary napkins and the like.

"Diaper" refers to an absorbent article generally worn by infants and incontinent persons about the lower torso.

"Disposable" is used herein to describe articles that are generally not intended to be laundered or otherwise restored or reused (i.e., they are intended to be discarded after a single use and, preferably, to be recycled, composted or otherwise disposed of in an environmentally compatible manner).

"Comprise," "comprising," and "comprises" is an open ended term that specifies the presence of what follows e.g. a component but does not preclude the presents of other features, elements, steps or components known in the art, or disclosed herein.

Preferably the carrier layer is a web material. The term "web material" refers to an essentially endless material in one direction, i.e. the longitudinal extension, or the length, or the x-direction in Cartesian coordinates relative to the web material. Included in this term is an essentially unlimited sequence of pieces cut or otherwise separated from an essentially endless material. Often, though not necessarily, the web materials will have a thickness dimension (i.e. the z-direction) which is significantly smaller than the longitudinal extension (i.e. in x-direction). Typically, the width of web materials (the y-direction) will be significantly larger than the thickness, but less than the length. Often, though not necessarily, the thickness and the width of such materials is essentially constant along the length of the web. Without intending any limitation, such web materials may be cellulosic fiber materials, tissues, woven or non-woven materials and the like. Typically, though not necessarily, web materials are supplied in roll form, or on spools, or in a folded state in boxes. The individual deliveries may then be spliced together to form the essentially endless structure. A web material may be composed of several web materials, such as multilayer non-woven, coated tissues, non-woven/film laminates. Web materials may comprise other materials, such as added binding material, particles, hydrophilizing agents and the like.

In the present invention the particulate material preferably comprises absorbent gelling material. The terms "absorbent gelling material" or "AGM", "super absorbent material" or "SAM", "superabsorbent", "absorbent polymer material" are used herein interchangeably, and refer to polymeric material that can absorb at least 10 times (and typically at least 15 times, or at least 20 times) their weight of an aqueous 0.9% saline solution as measured using the Centrifuge Retention Capacity test (Edana 441.2-02), i.e. having a CRC of at least 10 g/g, and typically at least 15 g/g or at least 20 g/g. Absorbent gelling material may be blended with other components, such as pulp fibres or "fluff", but preferably absorbent gelling materials alone are fed in the process of the present invention through the hopper.

According to one embodiment of the present invention, the particulate material (12) may be held in the recesses (22) by means of a vacuum applied to the inner side of the transfer device (18), in combination with suction holes in (the bottom) of the recesses (22), to apply the vacuum suction to the particulate material. The vacuum is preferably released just before or at the deposition zone, e.g. the point where the transfer device (18) is adjacent to the carrier layer (24). The vacuum (60) may be any vacuum pressure such as for example at least 4 kPa, preferably at least 10 kPa, or even at least 20 kPa.

The vacuum (60) may be provided by providing a plurality of vacuum chambers in the transfer device (18) (e.g. in its interior), where vacuum can be applied or released (connected or disconnected), depending on the position thereof in the process, e.g. when the vacuum chamber reaches the deposition zone, the vacuum may be disconnected and the particulate material (12) can flow from the transfer device (18) to the carrier layer (24), and when the chamber reaches the meeting point where the particulate material (12) flows from the feeder (10) to the recesses (22), the vacuum is applied (connected).

The rate of gas input may be approximately balanced with the rate of gas withdrawn through the print roll by the vacuum.

Additional air pressure may be applied to the particulate material (12) close to or at the deposition zone, to ensure that the material flows from the reservoir (22) to the carrier layer (24).

In another embodiment, a three dimensional plate may be employed to maintain the particulate material (12) within the recesses (22) while the particulate material (12) is being transferred. The plate is positioned adjacent to the feeder (10), downstream from the meeting point/area, and is positioned adjacent to, and in close proximity to, the transfer device (18). Thus, the feeder (10) is positioned before the plate, in direction of the process, e.g. in the direction of movement of the transfer device (18) (i.e. machine direction). Thus, it should be understood that at least part of the particulate material (12) contacts the surface of the transfer device (18) prior to contacting the first surface area of the plate.

Further details of the three dimensional plate are disclosed in EP-A-2 329 803, published on Jul. 8, 2011, and incorporated herein by reference.

The embodiments described above, namely the vacuum embodiment and the three-dimensional plate embodiment, may be combined in a single process/apparatus.

In one embodiment, the hopper (10) may be vibrated, for example by means of an electro-magnetic vibrator connected to the wall of the hopper (10). Vibration of the hopper (10), in some circumstances, and especially at higher process speeds, further helps to improve filling of the recesses. The vibration frequency may be from 10-500 Hz, more preferably from 30-70 Hz, and most preferably about 50 Hz. In another embodiment, the bulk of the particulate material may be vibrated by an internal vibrator.

The process speed may be conveniently defined by reference to the linear speed of the carrier layer (24). Note that the linear speed of the carrier layer (24) corresponds approximately to the tangential speed of the printing roll (18) as the printing roll (18) and the carrier layer (24) are approximately, but not necessarily exactly, matched for speed at the deposition zone. The linear speed of the carrier layer (24) may be at least 4.5 m/s, or at least 6 m/s, or at least 8 m/s, or at least 10 m/s. Such process speeds enable absorbent articles, or components thereof, to be manufactured at the rate of at least 1000, or at least 1200, or at least 1400 parts per minute, or higher.

The process shown in FIGS. 1 and 2 and described above may be operated with and without air-assisted filling. Trials were carried out at a process speed of 1400 parts per minute and a vacuum within the print roll of 20 kPa. The average loading of AGM per absorbent article, without any air-assisted filling used, was 6.5 grams. The average loading of AGM per absorbent article with air-assisted filling was 8 grams.

The invention claimed is:

1. A process for depositing particulate material in a predetermined pattern onto a carrier layer comprising the steps of:
feeding the particulate material under gravity from a hopper to a discharge zone containing a feed opening;
supplying a gas under pressure to the bulk of particulate material within the hopper discharge zone, wherein the gas is discharged in a direction from the interior of the hopper toward a surface of a transfer device;
transferring the particulate material through the feed opening to an outer surface of the transfer device, wherein the outer surface of the transfer device contains a pattern of particulate-receiving recesses;
rotating the transfer device to a deposition zone and transferring the particulate material to a carrier layer.

2. The process according to claim 1, wherein the gas is supplied under pressure within the bulk of particulate material within the hopper discharge zone.

3. The process according to either of claim 2, wherein the gas under pressure is air.

4. The process according to claim 1, comprising of retaining the particulate material within the particulate-receiving recesses by vacuum.

5. The process according to claim 4, wherein the vacuum is between about 4 kPa and about 25 kPa.

6. The process according to claim 1, comprising retaining the particulate material within the particulate-receiving recesses by a plate adjacent to, and in close proximity to, the surface of the transfer device.

7. The process according to claim 1, comprising vibrating the hopper at a frequency of from about 10 to about 500 Hz.

8. The process according to claim 7, wherein the frequency of vibrating the hopper is from about 30 to about 70 Hz.

9. The process according to claim 1, wherein the particulate material is absorbent gelling material.

10. A process for depositing particulate material in a predetermined pattern onto a carrier layer comprising the steps of:
feeding the particulate material under gravity from a hopper to a discharge zone containing a feed opening;
supplying a gas under pressure to the bulk of particulate material within the hopper discharge zone, wherein the gas is supplied by a conduit extending into the hopper;
transferring the particulate material through the feed opening to the surface of a transfer device, wherein the outer surface of the transfer device contains a pattern of particulate-receiving recesses;
rotating the transfer device to a deposition zone and transferring the particulate material to a carrier layer.

11. The process of claim 10, wherein the gas is supplied under pressure within the bulk of particulate material within the hopper discharge zone.

12. The process of claim 10, wherein the conduit comprises one or more holes, wherein the one or more holes are positioned such that the gas flows in a direction toward the outer surface of the transfer device.

13. The process of claim 10, wherein the gas aids in filling the particulate-receiving recesses.

14. The process according to claim 10, comprising retaining the particulate material within the particulate-receiving recesses by vacuum.

15. The process according to claim 10, wherein the conduit extends through a wall of the hopper to supply gas within the hopper.

16. A process for depositing particulate material in a predetermined pattern onto a carrier layer comprising the steps of:

feeding the particulate material under gravity from a hopper to a discharge zone containing a feed opening;

supplying a gas under pressure to the bulk of particulate material within the hopper discharge zone, wherein the gas is supplied by a conduit extending into the hopper, wherein the conduit comprises one or more holes configured to direct the gas toward a transfer device;

transferring the particulate material through the feed opening to an outer surface of the transfer device, wherein the outer surface of the transfer device contains a pattern of particulate-receiving recesses;

rotating the transfer device to a deposition zone and transferring the particulate material to a carrier layer.

17. The process of claim 16, wherein the gas is supplied under pressure.

18. The process of claim 16, wherein the gas aids in filling the particulate-receiving recesses.

19. The process according to claim 16, comprising vibrating the hopper at a frequency of from about 10 to about 500 Hz.

20. The process of claim 16, comprising retaining the particulate material within the particulate-receiving recesses by a plate adjacent to, and in close proximity to, the surface of the transfer device.

* * * * *